(12) United States Patent
Runeman et al.

(10) Patent No.: US 6,462,252 B1
(45) Date of Patent: Oct. 8, 2002

(54) REDUCTION OF UNWANTED SIDE-EFFECTS DURING USE OF ABSORBENT ARTICLES BY MEANS OF PH-CONTROL

(75) Inventors: Bo Runeman, Jonsered; Ulla Forsgren-Brusk, Pixbo, both of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/446,182

(22) PCT Filed: Jun. 10, 1998

(86) PCT No.: PCT/SE98/01111
§ 371 (c)(1),
(2), (4) Date: Mar. 8, 2000

(87) PCT Pub. No.: WO98/57677
PCT Pub. Date: Dec. 23, 1998

(30) Foreign Application Priority Data

Jun. 17, 1997 (SE) ............................... 9702298

(51) Int. Cl.[7] ............................... A61F 13/15

(52) U.S. Cl. ....................... 604/360; 604/375

(58) Field of Search ................. 604/358, 360, 604/367, 375, 374

(56) References Cited

U.S. PATENT DOCUMENTS

| 3,794,034 A | | 2/1974 | Jones, Sr. | |
| 3,935,862 A | * | 2/1976 | Kraskin | ...................... 128/287 |
| 4,685,909 A | * | 8/1987 | Berg et al. | ................... 604/360 |
| 5,669,894 A | * | 9/1997 | Goldman et al. | ........... 604/368 |

FOREIGN PATENT DOCUMENTS

| EP | 0 202 126 | 11/1986 |
| WO | WO 93/15702 | 8/1993 |

* cited by examiner

Primary Examiner—Aaron J. Lewis
Assistant Examiner—Jamisue Webb
(74) Attorney, Agent, or Firm—Young & Thompson

(57) ABSTRACT

Absorbent articles such as diapers, incontinence protectors, sanitary napkins, wound dressings and similar articles which are applied in contact with skin, and methods which make it possible to use an article for an extended period of time without the appearance of unwanted side-effects such as, for instance, growth of undesirable microorganisms. The absorbent body in the absorbent article comprises a pH-controlling substance in the form of a partially neutralized super-absorbent material in such a manner that the pH in the absorbent article after wetting is in the interval 3.5–4.9. Growth of undesirable strains of microorganisms is prevented and unwanted side-effects resulting from use of the article are reduced.

11 Claims, 1 Drawing Sheet

REDUCTION OF UNWANTED SIDE-EFFECTS DURING USE OF ABSORBENT ARTICLES BY MEANS OF PH-CONTROL

CROSS REFERENCE TO RELATED APPLICATION

This is the 35 USC 371 national stage of International Application PCT/SE98/01111, filed on Jun. 10, 1998, which designated the United States of America.

TECHNICAL FIELD

The present invention relates to absorbent articles such as diapers, incontinence protectors, sanitary napkins, wound dressings and similar articles which are applied against skin, and concerns methods aiming at the reduction of unwanted side-effects which sometimes occur during use of said articles.

1. Background

Absorbent articles of this kind are known in a number of different types. Conventionally, the absorbent body in these articles is produced by dry-defibration of cellulose pulp from, for instance, rolls, bales, or sheets and converting the pulp into a web of fluffed pulp sometimes with the admixture of what is known as superabsorbents, which are polymers with the ability to absorb several times their own weight of water or body fluids.

All uses of products which are applied against skin may lead to unwanted side-effects. These may occur as a result of occlusion, moisture, mechanical, microbial, and enzymatic factors which all, to different degrees, interact and amplify the influence of each other and may cause different forms of skin irritation and primary or secondary skin infections which sometimes occur in users of said articles. An increase in pH is a normal phenomenon during use of absorbent articles in contact with skin. However, several unwanted side-effects may occur as a result of, or in connection with, a pH-increase. One example of an unwanted side-effect of this kind is irritational contact dermatitis which exhibits a connection with the surface-pH of skin. Factors Predisposing Cutaneous Irritation, Wilhelm K-P et al, Dermatologic Clinics 8, No. 1, 1990.

Another example of unwanted effects is the activity of enzymes such as lipases and proteases which exhibit a strongly pH-dependent activity which increases with increasing pH. The skin starts to decompose and becomes sensitive to mechanical forces and bacterial attacks. Etiologic Factors in Diaper Dermatitis: The Role of Urine, Berg R. W. et al, Pediatric. Dermatology. 3, No. 2, 1986.

Another example of unwanted side-effects is that some bacteria such as Proteus can metabolise substances in urine and other body fluids and produce odorous substances such as ammonia and amines, which also raises the pH. At a high pH, the equilibrium for many odorous substances is shifted so that more volatile components are formed, resulting in a stronger odour than at a low pH.

An absorbent article such as a diaper, or the like provides an environment for micro-organisms which comprises access to moisture, nutrients, and heat. An unwanted side-effect of this is that growth of bacteria is promoted in such an environment. High numbers of bacteria constitute a risk of the appearance of infections. Moreover, a high presence of bacteria constitutes an increased risk for the creation of unpleasant odours caused by the formation of different substances, resulting from biological or chemical decomposition of components in body fluids such as, for instance, urine or menses.

Micro-organisms which may be associated with the occurrence of problems when using products in contact with skin may be of different types. Examples of micro-organisms which cause odour and those which constitute a risk for urinary tract infections are *Proteus mirábilis, Proteus vulgaris, Echerichia coli*, Enterococcus and Klebsiella.

Examples of micro-organisms which are associated with skin-infections and other skin problems are *Candida albicans* and Staphylococcus sp. and Streptococcus sp.

2. Related Art

It is known that a low pH is advantageous in order to reduce the occurrence of negative effects on skin.

Different ways of solving the described problems have been suggested. In the American patent U.S. Pat. No. 3,794,034 the importance of the pH in an absorbent article is described as well as the impregnation of an absorbent article with buffering substances which aid in keeping the pH in the article between 3.5 and 6.0, which is advantageous both for inhibiting the growth of unwanted bacteria and, in connection therewith, the creation of unwanted odours, and for avoiding negative effects on skin.

In the European patent 0,311,344 pH-control in an absorbent article is disclosed, wherein the buffering properties are obtained by using a partially neutralised superabsorbent material. In order to achieve sufficient inhibition of the growth of unwanted bacteria in the article, a separate bacteria inhibiting substance has also been added. The European patent EP 0,316,518 discloses buffering of pH in an absorbent article by using a polymeric organic acid.

One drawback in using bacteria suppressing agents, as described in EP 0,311,344, is that these agents are often selective and may be associated with risks, for instance in the form of allergenic properties or negative ecological consequences in garbage handling. Furthermore, the use of this type of agents may involve a risk that resistant strains of micro-organisms arise.

In EP 0,316,518 an absorbent article is disclosed, comprising a pH-controlling substance in the form of a partially neutralised superabsorbent material. It is stated that pH in the absorbent article is in the interval 5–6. However, this is not a sufficiently low pH in order to obtain a sufficient inhibition effect on the micro-organisms which are present since the majority of micro-organisms require a pH below 5 in order to be affected to a significant degree.

One difficulty when evaluating the influence of different components on the pH in absorbent articles of the aforementioned kind is that the degree of acidity in cellulose fluff pulp varies depending on the production method. Chemical cellulose pulp (CP) varies between pH 6–8.5 and chemical thermomechanical cellulose pulp (CTMP) varies between 5.5–8.5. Variations outside said intervals also occur.

OBJECT OF THE INVENTION

The object of the present invention is to achieve an absorbent article of the kind mentioned in the introduction which makes it possible to use the article during a longer period of time without the appearance of undesired side effects such as unpleasant odour, increased risk of infections or negative skin effects which are due to the growth of micro-organisms resulting from an unwanted raise in skin-pH, or from other reasons.

DESCRIPTION OF THE INVENTION

An absorbent article of the kind mentioned in the introduction, wherein the problems connected with using the article for an extended period of time have been substantially removed, has been achieved through the invention with an absorbent body in the absorbent article comprising a pH-controlling substance in the form of a partially neutralised superabsorbent material and in that pH in the absorbent article after wetting is in the interval 3.5–4.9, whereby growth of unwanted strains of micro-organisms is restricted and the occurrence of unwanted side effects resulting from the use of the article is reduced.

It has been shown that if the absorbent body in an absorbent article comprises a pH-controlling substance in the form of a partially neutralised superabsorbent material which after wetting creates a pH in the absorbent article which is in the interval 3.5–4.9, and preferably 4.1–4.7, a significant inhibition effect on the growth of unwanted micro-organisms is obtained. The inhibition effect is based on the fact that many micro-organisms have an activity which is strongly pH-dependent and decreases with decreasing pH, which means that a decrease in pH leads to a decrease in activity in most micro-organisms which, in turn, leads to a decrease of bad smell as well as negative effects on skin in the form of skin-irritation and primary or secondary skin-infections and a generally lower risk of infections.

Enzymes, such as lipases and proteases have an activity which is strongly pH-dependent and decreases with decreasing pH, which means that a decrease in pH will also lead to a decrease in enzymatic activity and an accompanying reduction in negative skin effects.

An absorbent body containing absorbent material and absorbed fluid is a heterogeneous system from a pH point of view. The system may contain superabsorbent material, fibres and liquid containing several kinds of ions. In order to obtain reproducible pH-values, measurements must be made in several places in the absorbent body and the mean value calculated.

An absorbent body in accordance with the invention may also comprise other absorbent materials besides a partially neutralised superabsorbent material, for instance fluffed cellulose pulp. It has proven advantageous to use a partially neutralised superabsorbent material as above in combination with fluffed cellulose pulp having a pH below 7, preferably below 6 which gives a further improved effect.

A suitable fluffed cellulose pulp may consist of a chemical thermo-mechanical cellulose pulp having a pH=2.5–8.5, preferably 2.5–6.5 and most preferably 2.5–5.5, or of a chemical cellulose pulp having a pH=2.5–8.5, preferably 2.5–8.0 and most preferably 2.5–7.0.

In order to obtain a suitable degree of acidity in the cellulose pulp, its pH may be controlled during the production process, for instance by adding an acidifying substance. This added substance may, for instance, consist of SO2-water. In this way, it is also possible to neutralise NaOH which may occur in the pulp. Another way of achieving a suitable degree of acidity in the cellulose pulp is to add a suitable acid after production of the pulp.

A suitable, partially neutralised superabsorbent material may, for instance, consist of a cross-linked poly-acrylate of the kind which is described in the European patent EP 0 391 108 in the name of Cassella AG. Other types of superabsorbent material than the above indicated, and having corresponding properties, may be used. A suitable proportion of superabsorbent material in the article is 5–100%, preferably 15–50%, and most preferably 15–50%. The proportion of superabsorbent material which has been stated to be preferred relates to areas of the article which will absorb the major part of the fluid and, consequently, does not concern end-portions or edge-portions or similar parts of the article since such parts thereof mostly do not significantly contribute to the absorptive function of the article.

Examples of the relation between the degree of neutralisation and pH in the superabsorbent material are given below.

| Degree of neutralisation % | pH |
| --- | --- |
| 18 | 4.0 |
| 25 | 4.3 |
| 30 | 4.5 |
| 35 | 4.7 |
| 45 | 5.0 |
| 60 | 5.5 |

From the table it can be learned that the degree of neutralisation should normally be lower than 45% and preferably 35%. However, the degree of neutralisation should preferably be higher than approximately 20%.

An absorbent body in accordance with the invention, comprising a partially neutralised super-absorbent material in accordance with the invention may have somewhat lower absorption capacity when compared to a corresponding absorbent body containing a conventional super-absorbent material. Such a lowering of the absorption capacity may be compensated by increasing the amount of absorbent material to a corresponding degree.

An absorbent body in accordance with the invention, comprising a partially neutralised super-absorbent material may also comprise some type of conventional bacteria-inhibiting substance such as parabens or benzoic acid. Such bacteria inhibitors normally exhibit an increased effect at a lower pH.

SHORT DESCRIPTION OF DRAWINGS

The invention will in the following be described in more detail, with reference to a number of examples which are shown in the appended figures.

DESCRIPTION OF EXAMPLES

Figure 1:
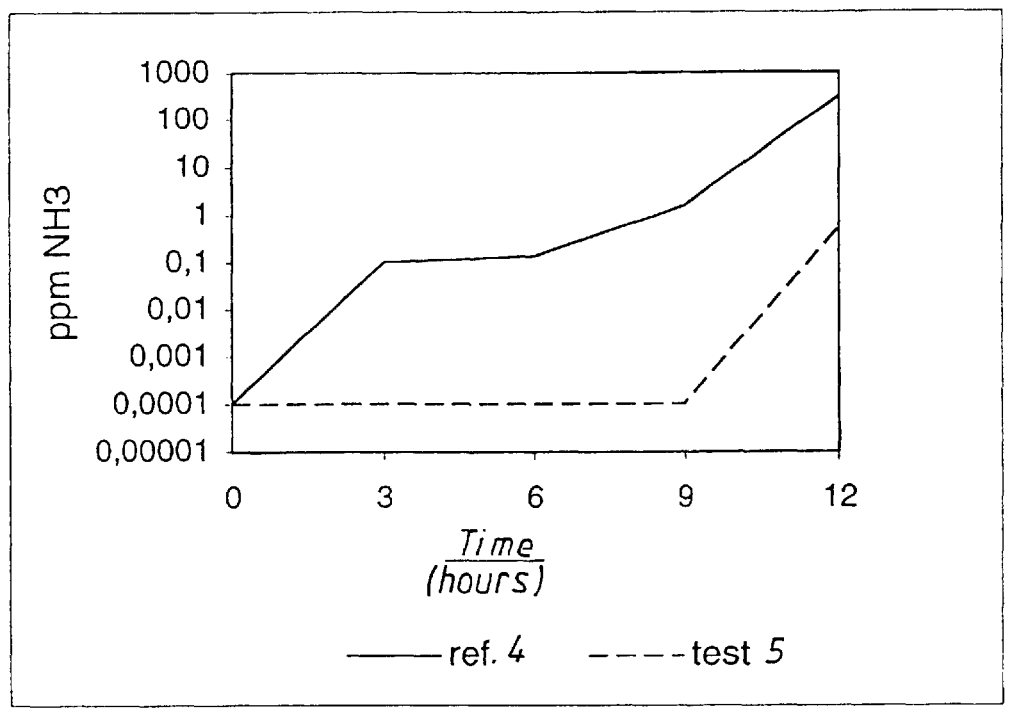
FIG. 1 shows in a diagram the formation of ammonia in a reference product compared with a product in accordance with the invention.

The following examples are intended to give a closer illustration of the effect in absorbent articles having an absorbent body comprising a combination of a partially neutralised super-absorbent material and cellulose pulp having a pH of 2.5–8.5 compared to conventional materials of a corresponding type.

TEST LIQUIDS

Test Liquid 1

A solution of 0.9% sodium chloride.

Test Liquid 2

Synthetic urine according to the description in, among other, EP 0,565,606 which can be obtained from Jayco Pharmaceuticals Co., Pennsylvania. The composition is 2 g/l KCl; 2 g/l $Na_2SO_4$; 0.85 g/l $(NH_4)H_2PO_4$; 0.15 g/l $(NH_4)_2HPO_4$; 0.19 g/l $CaI_2$ and 0.23 g/l $MgCl_2$. The pH in this composition is 6.0–6.4.

Test Liquid 3

Synthetic urine containing the following substances: KCl, NaCl, $MgSO_4$, $KH_2PO_4$, $Na_2HPO_4$, $NH_2CONH_2$. The pH in this composition is 6.0–6.5.

Test Liquid 4

Sterile synthetic urine to which has been added a growth medium for micro-organisms. The synthetic urine contains mono- and divalent cat- and anions and urea and has been prepared in accordance with the information in Geigy, Scientific Tables, vol 2, 8th ed. 1981 p. 53. The growth medium for micro-organisms is based on information of Hook- and FSA-media for entero-bacteria. The pH in this mixture is 6.6.

TEST METHODS

Method 1, Preparation of Absorbent Bodies for Test

Absorbent bodies were prepared using a slightly modified sample former according to SCAN C 33:80. Fluffed pulp and super-absorbent material of the desired type were weighed and a homogeneous mixture of fluffed pulp and super-absorbent material was subsequently introduced into a flow of air having a negative, pressure of approximately 85 mbar, through a pipe having a diameter of 5 cm and being equipped at the bottom with a metal net having a thin tissue placed thereon. The mixture of fluffed pulp and super-absorbent material was gathered onto the tissue on the metal net and thereafter constituted the absorbent body. The absorbent body was weighed and compressed to a bulk of 6–12 cm3/g. A number of absorbent bodies referred to as Reference product 1, Reference product 2, test product 1, test product 2, test product 3, test product 4, etc. having different compositions as described below were made. The amount of absorbent material in the single core and dual core absorbent bodies, respectively, was adjusted so that the single cores and dual cores had approximately the same absorption capacity.

Method 2, Measurement of pH in Cellulose Pulp

The pH in the cellulose pulp in the different test products was measured by determining the pH in a water extract from the pulp in accordance with SCAN P 14:65. 1.0 g air dry cellulose pulp was placed in a 100 ml glass container and 20 ml distilled water was added. After mixing, a further 50 ml of distilled water was added and the mixture was stirred for approximately 30 s and was left for 1 hour. The liquid was poured off and pH was determined with a glass electrode at 20–30° C. Two samples were prepared and the mean value was calculated.

Method 3, Measurement of pH in an Absorbent Body

An absorbent body having a diameter of approximately 50 mm was prepared according to method 1. A predetermined amount of Test liquid 1, 2 or 3 was added, 10 ml to a single core absorbent body and 20 ml to a dual core absorbent body, whereafter the absorbent body was left to swell for 30 minutes. Thereafter, pH was measured in the absorbent body using a surface electrode, Flat-bottomed Metrohm pH-meter, Beckman Ø12 or Ø72. Parallel measurements were performed on at least two different absorbent bodies. The pH was determined at 10 locations on each absorbent body and the mean value was calculated.

Method 4, Measurement of Bacteria Inhibition in Absorbent Bodies

Absorbent bodies were prepared in accordance with method 1. Single core, as well as dual core absorbent bodies were prepared. Test liquid 4 was prepared. Bacteria suspensions of each of *Escherichia coli* (*E.c.*), *Proteus mirábilis* (*P.m.*), *Enterococcus faecalis* (*E.f.*) were cultivated in nutritional bouillon 30° C. overnight. The graft cultures were diluted and the bacterial count was determined. The cultures were mixed in different proportions so that the final mixed culture contained approximately 104 organisms per ml test liquid 4. Test liquid 4 was added to a sterile sputum container 70.5×52 mm, volume 100 ml, and the absorbent body was placed upside-down in the container and was left to absorb liquid for 5 minutes, whereafter the container was turned and incubated at 35° C. for 0; 6 and 12 hours, respectively whereafter the bacterial count in the absorbent body was determined. The nutritional medium used was TGE agar for measurement of the total amount of bacteria and Drigalski agar for specific determination of *Escherichia coli* and *Proteus mirábilis*, and Slanetz Bartley agar for specific determination of *Enterococcus faecalis*.

Method 5, Measurement of Ammonia Content

Single core absorbent bodies were prepared in accordance with method 1. Test liquid and micro-organisms were added in accordance with method 5 whereafter the containers were incubated at 35° C. for 0; 3; 6 and 12 hours, whereafter samples were taken from the containers using a hand pump an a so called Dräger-pipe. The ammonia content was obtained as a colour change on a scale graded in ppm or volume-percent.

Method 6, Measurement of the Surface-pH of Skin

Test products were prepared by applying a backing of approximately 25 $g/m^2$ polyethylene and a topsheet of approximately 20 $g/m^2$ polypropylene nonwoven to absorbent bodies according to Ref. 3 and test 4, respectively. Test liquid 3 was added to the topsheet and was absorbed into the test product. The test products which were obtained in this manner were applied to the forearms of a test person and were left there for 24 hours. The procedure was repeated twice. The surface-pH of the skin at the place of contact was measured before application and after 24, 48 and 72 hours with Courage+Khazaka skin-pH-meter with a flat-bottomed Mettler-Toledo glass electrode 403/120.

TEST PRODUCTS

Reference product 1: Single core absorbent body having a total weight of 1 gram, prepared from a conventional super-absorbent material and a conventional chemical thermo-mechanical cellulose pulp with the ratio 15/85 weight-%.

Test product 1: Single core absorbent body having a total weight of 1 gram, prepared from a partially neutralised super-absorbent material with pH=4.2, in accordance with the invention, and a chemical thermo-mechanical cellulose pulp with pH=5.8 and with the ratio 15/85 weight-%.

Test product 2: Single core absorbent body having a total weight of 1 gram, prepared from a partially neutralised super-absorbent material with pH=4.2, in accordance with the invention, and a chemical thermo-mechanical cellulose pulp with pH 3.7 and with the ratio 15/85 weight-%.

Reference product 2: Dual core absorbent body. The upper core (uc) had a total weight of 1.2 grams and was prepared from a conventional super-absorbent material and a conventional chemical thermo-mechanical cellulose pulp with the ratio 12/88 weight-%. The lower core (lc) had a total weight of 1.1 grams and was prepared from a conventional super-absorbent material and a conventional chemical cellulose pulp with the ratio 12/88 weight-%.

Test product 3: Dual core absorbent body. The upper core (uc) had a total weight of 1.3 grams and was prepared from a partially neutralised super-absorbent material having a pH=4.5, in accordance with the invention, and a chemical thermo-mechanical cellulose pulp having a pH=5.8 and with the ratio 15/85 weight-%. The lower core (lc) had a total weight of 1.2 grams and was prepared from a partially neutralised super-absorbent material having a pH=4.5, in accordance with the invention, and a chemical cellulose pulp having a pH=6.3 and with the ratio 15/85 weight-%.

Reference product 3: Single core absorbent body having a total weight of 1 gram, prepared from a conventional super-absorbent material and a conventional chemical cellulose pulp, with the ratio 15/85 weight-%.

Test product 4: Single core absorbent body having a total weight of 1 gram, prepared from a partially neutralised super-absorbent material with pH=4.2, in accordance with the invention, and a conventional chemical cellulose, with the ratio 15/85 weight-%.

Reference product 4: Single core absorbent body having a total weight of 1 gram, prepared from a conventional super-absorbent material and a chemical thermo-mechanical cellulose pulp with pH=6.7, with the ratio 15/85 weight-%.

Test product 5: Single core absorbent body having a total weight of 1 gram, prepared from a partially neutralised super-absorbent material with pH=4.2, in accordance with the invention, and a chemical thermo-mechanical cellulose pulp with pH=6.7 and with the ratio 15/85 weight-%.

Test product 6: Dual core absorbent body. The upper core (uc) had a total weight of 1.3 grams and was prepared from a partially neutralised super-absorbent material having a pH=4.6, in accordance with the invention, and a chemical thermo-mechanical cellulose pulp having a pH=5.8 and with the ratio 15/85 weight-%. The lower core (lc) had a total weight of 1.2 grams and was prepared from a partially neutralised super-absorbent material having a pH=4.6, in accordance with the invention, and a chemical cellulose pulp having a pH=6.3 and with the ratio 15/85 weight-%.

TEST RESULTS

EXAMPLE 1

Table 1 shows that in a single core, conventional absorbent body according to reference product 1, good growth of micro-organisms prevails. The measurement was performed in accordance with Method 4.

TABLE 1

| time | Esherichia coli | Proteus mirabilis | Enterococcus faecalis |
|---|---|---|---|
| 0 hours | 3.3 | 3.1 | 3.1 |
| 6 hours | 7.0 | 6.4 | 7.1 |
| 12 hours | 9.2 | 9.1 | 8.3 |

EXAMPLE 2

Table 2 shows that in a single core absorbent body according to test product 1, good inhibition of the growth of micro-organisms is obtained. The measurement was performed in accordance with Method 4.

TABLE 2

| time | Esherichia coli | Proteus mirabilis | Enterococcus faecalis |
|---|---|---|---|
| 0 hours | 3.2 | 3.3 | 3.4 |
| 6 hours | 5.5 | 3.2 | 4.8 |
| 12 hours | 7.3 | 4.0 | 6.1 |

EXAMPLE 3

Table 3 shows that in a single core absorbent body according to test product 2, good inhibition of the growth of micro-organisms is obtained. The measurement was performed in accordance with Method 4.

TABLE 3

| time | Esherichia coli | Proteus mirabilis | Enterococcus faecalis |
|---|---|---|---|
| 0 hours | 3.4 | 3.3 | 3.5 |
| 6 hours | 3.2 | 2.6 | 3.6 |
| 12 hours | 2.8 | 2.0 | 3.5 |

EXAMPLE 4

Table 4 shows that in a dual core, conventional absorbent body according to reference product 2, good growth of micro-organisms prevails. The measurement was performed in accordance with Method 4.

TABLE 4

| | Esherichia coli | | Proteus mirabilis | | Enterococcus faecalis | |
|---|---|---|---|---|---|---|
| time | uc* | lc** | uc* | lc** | uc* | lc** |
| 0 hrs | 3.4 | 3.4 | 3.4 | 3.4 | 3.4 | 3.4 |
| 6 hrs | 6.8 | 7.0 | 6.0 | 6.7 | 6.7 | 6.2 |
| 12 hrs | 9.0 | 9.0 | 9.1 | 9.0 | 8.0 | 7.8 |

*uc = upper core, **uk = lower core

EXAMPLE 5

Table 5 shows that in a single core, absorbent body according to test product 3, good inhibition of the growth of micro-organisms is obtained. The measurement was performed in accordance with Method 4.

TABLE 5

| | Esherichia coli | | Proteus mirabilis | | Enterococcus faecalis | |
|---|---|---|---|---|---|---|
| time | uc* | lc** | uc* | lc** | uc* | lc** |
| 0 hrs | 3.4 | 3.4 | 3.4 | 3.4 | 3.4 | 3.4 |
| 6 hrs | 5.1 | 5.6 | 3.3 | 4.2 | 4.4 | 4.5 |
| 12 hrs | 7.3 | 7.4 | 4.0 | 4.0 | 5.9 | 4.8 |

*uc = upper core, **lc = lower core

EXAMPLE 6

FIG. 1 shows that efficient delay of the development of ammonia is obtained in a single core absorbent body according to test product 5 when compared to a single core, conventional absorbent body, according to Reference product 4. The measurement was performed in accordance with Method 5.

EXAMPLE 7

Figure 2:
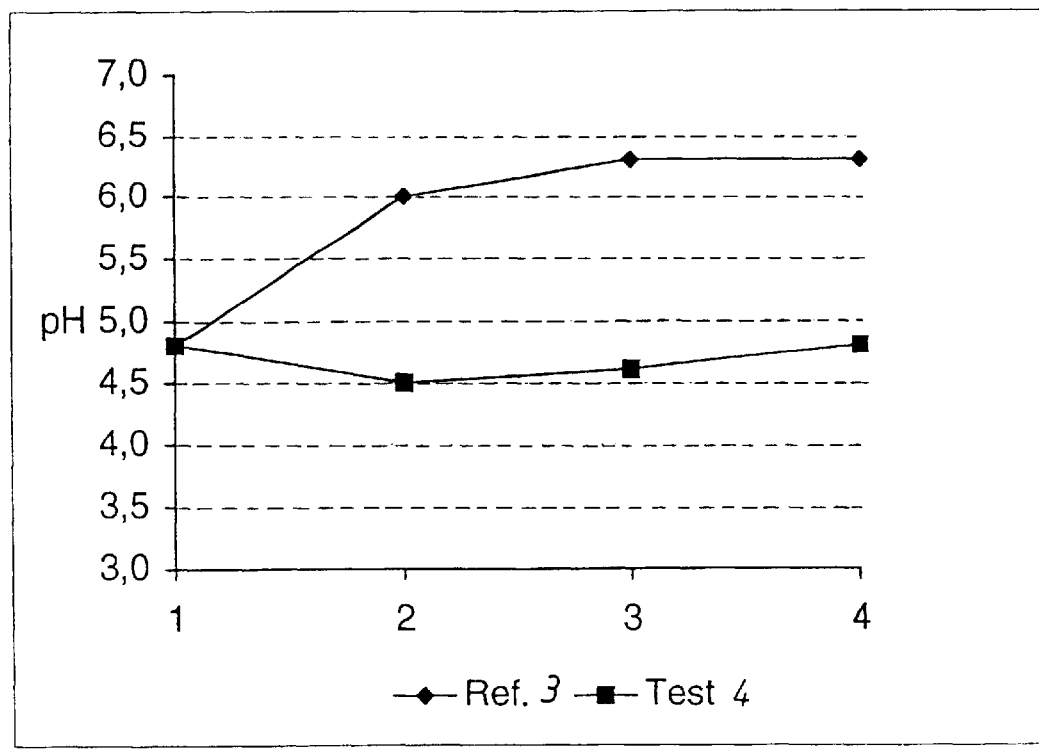
FIG. 2 shows in a diagram the surface-pH of the skin during use of a test product containing a conventional absorption body, compared with the use of a corresponding test product in accordance with the invention.

FIG. 2 shows that the surf ace-pH of skin after a period of use of a test product containing an absorbent body in accordance with the invention, test product 4, is stabilised at a lower level than after use of a corresponding test product containing a conventional super-absorbent material, according to Reference product 3, after addition of Test liquid 3. The measurement was performed in accordance with Method 6.

EXAMPLE 8

Table 6 shows that pH, when measured in a single core absorbent body, test product 1, in accordance with the invention, after addition of test liquid, lies within the effective pH-interval 3.5–4.9. The measurement was performed in accordance with Method 3.

TABLE 6

|    | Test Liquid 1 | Test Liquid 2 | Test Liquid 3 |
|----|---------------|---------------|---------------|
| pH | 4.29          | 4.42          | 4.54          |

EXAMPLE 9

Table 7 shows that pH, when measured in a dual core absorbent body, test product 6, in accordance with the invention, after addition of test liquid, lies within the effective pH-interval 3.5–4.9. The measurement was performed in accordance with Method 3.

TABLE 7

|        | Test Liquid 1 | Test Liquid 2 | Test Liquid 3 |
|--------|---------------|---------------|---------------|
| pH uc* | 4.72          | 4.83          | 4.80          |
| pH lc* | 4.75          | 4.74          | 4.73          |

The invention shall-not be considered to be restricted to the embodiments described herein. Accordingly, a number of further variants and modifications are conceivable within the scope of the appended claims.

What is claimed is:

1. An absorbent article intended to be worn in contact with the skin of a wearer, and comprising:

an absorbent body comprising a) a pH-controlling substance in the form of a partially neutralized super-absorbent material having a degree of neutralization of less than 45%, and b) a fluffed cellulose pulp having a pH below 7;

said pH-controlling substance being located in said absorbent body, such that during use of the absorbent article in contact with the skin and after wetting, the pH inside the absorbent article ranges from 3.5 to 4.9.

2. The absorbent article according to claim 1, wherein during use of the absorbent article in contact with the skin and after wetting, the absorbent article has an internal pH which ranges from 4.1 to 4.7.

3. The absorbent article according to claim 1, wherein the pH has been obtained in a pulp manufacturing process by adding an acidifying agent.

4. The absorbent article according to claim 1, wherein the pH has been obtained by adding an acidifying agent in a separate step after a pulp manufacturing process.

5. The absorbent article according to claim 1, wherein the fluffed cellulose pulp is a chemical cellulose pulp (CP).

6. The absorbent article according to claim 5, wherein the chemical cellulose pulp has a pH from 2.5 to 7.0.

7. The absorbent article according to claim 1, wherein the fluffed cellulose pulp is a chemical thermo-mechanical cellulose pulp (CTMP).

8. The absorbent article according to claim 7, wherein the chemical thermo-mechanical cellulose pulp has a pH from 2.5 to 6.5.

9. The absorbent article according to claim 8, wherein the chemical thermo-mechanical cellulose pulp has a pH from 2.5 to 5.5.

10. The absorbent article according to claim 8, wherein the pH of the chemical thermo-mechanical cellulose pulp has been obtained by adding an acidifying agent.

11. The absorbent article according to claim 8, wherein the pH of the chemical thermo-mechanical cellulose pulp has been obtained by adding an acidifying agent in a separate step after a pulp manufacturing process.

* * * * *